United States Patent
Chan et al.

(10) Patent No.: US 10,426,158 B2
(45) Date of Patent: Oct. 1, 2019

(54) POLYMERIC SORBENT FOR REMOVAL OF IMPURITIES FROM WHOLE BLOOD AND BLOOD PRODUCTS

(75) Inventors: Phillip P. Chan, Cherry Hill, NJ (US); Vincent J. Capponi, Monmouth Junction, NJ (US); Thomas D. Golobish, Princeton, NJ (US); Humayra Begum Ali, Princeton, NJ (US)

(73) Assignee: CytoSorbents Corporation, Monmouth Junction, NJ (US)

( * ) Notice: Subject to any disclaimer, the term of this patent is extended or adjusted under 35 U.S.C. 154(b) by 808 days.

(21) Appl. No.: 14/238,548

(22) PCT Filed: Aug. 10, 2012

(86) PCT No.: PCT/US2012/050295
§ 371 (c)(1),
(2), (4) Date: May 22, 2014

(87) PCT Pub. No.: WO2013/025483
PCT Pub. Date: Feb. 21, 2013

(65) Prior Publication Data
US 2015/0118673 A1  Apr. 30, 2015

Related U.S. Application Data

(60) Provisional application No. 61/523,170, filed on Aug. 12, 2011.

(51) Int. Cl.
*A01N 1/02* (2006.01)
*B01J 20/26* (2006.01)
*B01J 20/28* (2006.01)
*C08F 236/20* (2006.01)

(52) U.S. Cl.
CPC ............ *A01N 1/021* (2013.01); *B01J 20/267* (2013.01); *B01J 20/2808* (2013.01); *B01J 20/28016* (2013.01); *B01J 20/28073* (2013.01); *B01J 20/28076* (2013.01); *B01J 20/28083* (2013.01); *B01J 20/28085* (2013.01); *C08F 236/20* (2013.01)

(58) Field of Classification Search
None
See application file for complete search history.

(56) References Cited

U.S. PATENT DOCUMENTS

| | | |
|---|---|---|
| 4,082,509 A | 4/1978 | Talcott |
| 4,846,786 A | 7/1989 | Freed et al. |
| 6,114,466 A | 9/2000 | Davankov et al. |
| 6,162,469 A | 12/2000 | Atarashi et al. |
| 6,559,290 B1 * | 5/2003 | Nakatani ............... B01D 15/00 210/650 |
| 2007/0297858 A1 * | 12/2007 | Imbrie ................... B09C 1/002 405/128.45 |
| 2008/0119576 A1 | 5/2008 | Young et al. |

FOREIGN PATENT DOCUMENTS

| | | |
|---|---|---|
| DE | 10157569 | 6/2003 |
| JP | 2001508775 | 7/2001 |

OTHER PUBLICATIONS

Elert (<http://hypertextbook.com/facts/2004/MichaelShmukler.shtml> 2004, Accessed Jan. 3, 2017).*
Gokmen et al., "Porous Polymer Particles—A Comprehensive Guide to Synthesis, Characterization, Functionalization and Applications", Progress in Polymer Science, 2012, 37(3), 365-405.
Sigma-Aldrich, Amberlite XAD16HP pkg of 1000g, http://www.sigmaaldrich.com/catalog/product/supelco/13357u?lang=en&region=US.

* cited by examiner

Primary Examiner — Thomas J. Visone
(74) Attorney, Agent, or Firm — BakerHostetler

(57) ABSTRACT

The invention concerns methods of treating stored blood and blood products maximizing shelf life and/or minimizing transfusion related complications such as non¬ hemolytic transfusion reactions such as fever, transfusion-related acute lung injury (TRALI), transfusion associated dyspnea (TAD), and allergic reactions by removing undesirable molecules in the blood and blood products milieu through use of a sorbent.

36 Claims, 7 Drawing Sheets

POLYMERIC SORBENT FOR REMOVAL OF IMPURITIES FROM WHOLE BLOOD AND BLOOD PRODUCTS

CROSS-REFERENCE TO RELATED APPLICATIONS

This application is the National Stage of international application number PCT/US2012/050295 filed Aug. 10, 2012, which claims the benefit of U.S. provisional application No. 61/523,170, filed Aug. 12, 2011, the disclosures of which are incorporated herein by reference in their entireties.

TECHNICAL FIELD

The present invention concerns compositions and methods useful in the removal of cytokines, bioactive lipids, free hemoglobin, membrane or cellular degradation products, inflammatory mediators, vasoactive substances, foreign antigens, and antibodies from blood and blood products.

BACKGROUND

The transfusion of whole blood or derivatives of whole blood ("blood products") are literally the lifeblood of patients with a range of conditions from severe trauma to surgery to cancer. According to the American Red Cross, there are more than 14 million packed red blood cell (pRBC) transfusions per year in the United States with 1 in every ten admissions to US hospitals requiring a blood transfusion on average. A similar number of transfusions of other fractions of whole blood, or blood products, such as platelets, white blood cells, plasma, albumin, immunoglobulins, clotting factors and cryoprecipitate, are administered each year. The critical need for blood extends to the military, where logistics of blood transport and storage are complicated and 8% of all hospital admissions during Operation Iraqi Freedom required massive transfusions, defined as more than 10 units of blood in the first 24 hours. Whole blood and blood products will be collectively referred to herein as "blood".

Blood has a limited life span. A typical pRBC unit has a usable life of only 42 days while platelets must be used within 5 days of donation. This, coupled with the high demand for blood, has led to periodic blood shortages. But many medical experts believe fresh blood should be used even sooner, within 2-4 weeks. Retrospective studies have implicated transfusions of "older" blood with an increased risk of non-hemolytic transfusion reactions such as fever, transfusion related acute lung injury (TRALI), transfusion associated dyspnea (TAD), allergic reactions, infection, death and other complications. In one of these studies, the risk of in-hospital death increased by 2% for each day a packed red cell unit aged. Because of this, extending the useful life of blood products and improving the quality of blood would be helpful.

SUMMARY

In one embodiment of the invention, transfusion related complications such as non-hemolytic transfusion reactions such as fever, transfusion related acute lung injury (TRALI), transfusion associated dyspnea (TAD), allergic reactions are mitigated by removing undesirable molecules from blood through use of a sorbent. Use of a sorbent to remove undesirable products from transfusable blood can also extend the useful shelf life of this blood by, for example, removing undesirable products that accumulate during storage. These undesirable products found in blood are herein collectively referred to as Biologically Active Molecules (BAM)s. BAMs are defined as any substance or molecule that can, by itself or in combination with other BAMs, cause a biological, cellular or physiologic process. During blood transfusions, BAMs can elicit an undesirable physiologic response in the recipient of the transfused blood, such as TRALI, TAD, and others. For example, anti-human leukocyte antigen antibodies are BAMs linked to severe cases of TRALI. Prions, another example of a BAM, can cause Creutzfeldt-Jakob disease or subacute spongiform encephalopathy. A subset of BAMs are biological response modifiers (BRMs), which are substances that have an effect on the immune system. These include, for example, cytokines, chemokines, antibodies, glycoproteins, and growth factors. Cytokines found in transfusable blood can cause fever in the recipient.

In another embodiment, BAMs present in blood and blood products such as drugs, inflammatory mediators and stimulators such as cytokines, chemokines, interferons, nitric oxide, thromboxanes, leukotrienes, platelet-activating factor, prostaglandins, glycoproteins, kinins, kininogens, complement factors, cell-adhesion molecules, superantigens, monokines, free radicals, proteases, arachidonic acid metabolites, prostacyclins, beta endorphins, myocardial depressant factors, anandimide, 2-arachadonylglycerol, tetrahydrobiopterin, histamine, bradykinin, soluble CD40 ligand, serotonin, hemoglobin, bioactive lipids, antibodies, antigens, prions, toxins, endotoxins, membrane or cellular components, and other BRMs are removed by the sorbent. These BAMs may have been present in the donor's blood at the time the blood donation was made or may develop over time as the blood is processed, or is in storage, or as part of the aging process.

Suitable sorbents include biocompatible polymers. Certain polymers are hemocompatible. Some biocompatible polymers are supplied as a slurry, or suspension, or dry powder or other dry particulate capable of being wetted.

In some embodiments, a blood storage bag or suitable blood container may be used such that the polymeric sorbents are in the form of beads, such that the beads are neutrally buoyant in blood. Suitable buoyant beads of polymeric sorbents will have a density that is comparable to the composition (fluid) in which the beads reside.

In another embodiment, sorbents are neutrally buoyant in blood so that BAMs can be removed throughout the whole volume of blood without the need for mixing over time.

In some embodiments, the donated blood is treated with a sorbent to remove undesirable antibodies such as anti-leukocyte antibodies, and anti-human leukocyte antigen antibodies, at the time of donation, during storage, or at the point of use.

In another embodiment, increasing the apparent density of the beads by adding heavier heteroatoms to the polymer matrix allows the synthesis of neutrally buoyant beads in relation to Packed Red Blood Cells (RBC's). This can be accomplished by suspension, seed, dispersion, precipitation, multistage, membrane/microchannel emulsification and microfluidic polymerizations to form neutrally buoyant porous particles (Gokmen M T, Du Prez F E. Porous polymer particles—A comprehensive guide to synthesis, characterization, functionalization and applications. Prog Polym Sci 2012; 37:365-405).

In other embodiments, polymers comprise particles having a diameter in the range for 0.1 micron meters to 2 centimeters. Certain polymers are in the form of powder, beads or other regular or irregularly shaped particulates.

In certain embodiments, the polymer is made of particles having a diameter in the range for 0.1 micron meters to 2 centimeters, is porous, and has a pore structure that the total pore volume of pore size in the range of 50 Å to 40,000 Å is greater than 0.5 cc/g to 5.0 cc/g dry polymer.

Some preferred polymers comprise residues from one or more monomers or heteroatom containing monomers or mixtures there of selected from divinylbenzene and ethylvinylbenzene, styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythritol dimethacrylate, pentaerythritol trimethacrylate, pentaerythritol tetramethacrylate, pentaerythritol diacrylate, pentaerythritol triiacrylate, pentaerythritol tetraacrylate, dipentaerythritol dimethacrylate, dipentaerythritol trimethacrylate, dipentaerythritol tetramethacrylate, dipentaerythritol diacrylate, dipentaerythritol triacrylate, dipentaerythritol tetraacrylate, divinylformamide, 2-chlorostyrene, 3-chlorostyrene, 4-chlorostyrene, 2,6-dichlorostyrene, 4-vinylbenzyl chloride, 2-bromostyrene, 3-bromostyrene, 4-bromostyrene, 2-fluorostyrene, 3-fluorostyrene, 4-fluorostyrene, 2-trifluoromethylstyrene, 3-trifluoromethylstyrene, 4-trifluoromethylstyrene, 2,3,4,5,6-pentafluorostyrene, 4-vinyl-18-crown-6 benzene, 2-chloroacrylate, 2,2,2-trifluoromethylmethacrylate, 2-trifluoromethylacrylate, methyl 2-(chloromethyl) acrylate, methyl 2-(bromomethyl)acrylate, 1H, 1H, 2H, 2H-heptadecafluorodecyl acrylate, vinyl chloroacetate, and 2-chloroethyl vinyl ether.

In some embodiments, the polymer is a coated polymer comprising at least one crosslinking agent and at least one dispersing agent. The dispersing agent may be hemocompatible. The dispersing agents can be selected from chemicals, compounds or materials such as hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly(diethylaminoethyl acrylate), poly(vinyl alcohol), poly(N-vinylpyrrolidinone), salts of poly(methacrylic acid), and salts of poly(acrylic acid) and mixtures thereof the crosslinking agent selected from a group consisting of divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof. Preferably, the polymer is developed simultaneously with the formation of the coating, wherein the dispersing agent is chemically bound to the surface of the polymer.

Some embodiments of the invention use an organic solvent and/or polymeric porogen as the porogen or poreformer, and the resulting phase separation induced during polymerization yield porous polymers. Some preferred porogens are benzyl alcohol, cyclohexane, cyclohexanol, cyclohexanol/toluene mixtures, cyclohexanone, decane, decane/toluene mixtures, di-2-ethylhexylphosphoric acid, di-2-ethylhexyl phthalate, 2-ethyl-1-hexanoic acid, 2-ethyl-1-hexanol, 2-ethyl-1-hexanol/n-heptane mixtures, 2-ethyl-1-hexanol/toluene mixtures, isoamyl alcohol, n-heptane, n-heptane/ethylacetate, n-heptane/isoamyl acetate, n-heptane/tetraline mixtures, n-heptane/toluene mixtures, n-hexane/toluene mixtures, pentanol, poly(styrene-co-methyl methacrylate)/dibutyl phthalate, polystyrene/2-ethyl-1-hexanol mixtures, polystyrene/dibutyl phthalate, polystyrene/n-hexane mixtures, polystyrene/toluene mixtures, toluene, tri-n-butylphosphate, 1,2,3-trichloropropane/2-ethyl-1-hexanol mixtures, 2,2,4-trimethyl pentane (isooctane), trimethyl pentane/toluene mixtures, poly(propylene glycol)/toluene mixtures poly(propylene glycol)/cyclohexanol mixtures, and poly(propylene glycol)/2-ethyl-1-hexanol mixtures In one embodiment, the polymer is capable of sorbing protein molecules approximately 100 Daltons to about 1,000 Kilodaltons.

In another embodiment a porous polymer that sorbs small to midsize protein molecules equal to or less than 50,000 Daltons and excludes or reduces absorption of large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 100 Å to 1,000 Å (pore diameter) of the sorbent is smaller than 3:1.

In another embodiment a porous polymer that optimally sorbs midsize to large size protein molecules of approximately 300,000 Daltons and excludes or reduces absorption of very large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 1,000 Å to 10,000 Å (pore diameter) of the sorbent is smaller than 2:1

In another embodiment a porous polymer that optimally sorbs very large size protein molecules equal to or less than 1,000,000 Daltons (100 Daltons to 450,000 Daltons in some embodiments) and excludes or reduces absorption of very large blood proteins comprises the pore structure such that the total pore volume of pore size in the range of 50 Å to 40,000 Å are in the range of 0.5 cc/g to 5.0 cc/g dry sorbent. The sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 10,000 Å to 40,000 Å (pore diameter) of the sorbent is smaller than 3:1.

In some embodiments, the polymers may be derivatized. Some polymers may be modified with an antibody or ligand. Certain ligands specifically or non-specifically bind reactive biomolecules. Such polymer may be porous or solid.

In some embodiments, the composition is contained in a suitable blood container with the blood or blood products. In certain embodiments, the invention concerns a blood storage bag comprising any of the compositions discussed herein. In some embodiments, the sorbent is in a suitable container to hold blood and in direct contact with blood and blood products but incapable of escaping from the container. In some embodiments the composition is part of the storage container material that forms the container. In some embodiments, the composition is coated or deposited on the interior surface of the storage container and in direct contact with blood or blood products. In some embodiments the material is separated from the blood via membrane but fluid may pass through the membrane allowing BRMs to communicate with the composition but excluding cells such as white blood cells, red blood cells and platelets. Some methods further comprise separating the composition from the blood via filtration. In certain embodiments the filtration occurs while the blood is removed from the storage bag during transfusion to a patient. In some embodiments the sorbent in the blood container is in direct contact with the blood.

In other embodiments, the sorbent is structurally an integral part of the container material homogeneously dispersed throughout the container walls, or discretely sealed in multiple areas of the container providing zones of direct contact with the blood or blood products, or coated, deposited or attached to the inside walls of the container in direct contact with the blood or blood products.

Certain embodiments concern filters comprising any of the composition discussed herein. Some embodiments, concern a filter cartridge comprising any of the composition discussed herein. Some devices of the invention are blood filtration devices comprising a filter or filter cartridge comprising the any of the composition discussed herein.

In some embodiments the composition is contained in a filter and either the blood from the donor at the time of donation is passed through the filter before placement into a suitable blood container or the blood or blood products in the blood container pass through the filter during transfusion into the patient. For purposes of this invention, the term "sorb" is defined as "taking up and binding by absorption and adsorption".

Some sorbents have a skeletal density in the range of from about 1.0 g/ml to about 1.3 g/ml, or in some embodiments, 1.1 g/ml to about 1.3 g/ml. Certain sorbents have a skeletal density that is substantially the same as the density of the blood or blood product. In other embodiments, the sorbent polymeric bead is for sorbing impurities from blood comprising the any of the composition described herein where the sorbent polymeric bead has a neutral or near-neutral buoyancy in the stored blood or blood products.

In some embodiments, as used herein, "substantially the same" means plus or minus 10% of the referenced value. As used herein, "near-neutral buoyancy" means that the sorbent has substantially the same density as the stored blood or blood product.

In certain embodiments, the methods of the invention use a seed polymerization method including seed of polymers based on 100% hetero atom monomer and non hetero atom monomers such that the combination can lead to a neutrally buoyant system. Certain seed polymers are comprised of a mixture of hetero atom and non hetero atom monomer.

With some methods of the invention, the sorbent is in a suitable container to hold blood and in direct contact with blood and blood products but incapable of escaping from the container at a level that meets USP particulate as specified in IARC monograph 65. IARC (International Agency for Research on Cancer) Monographs identify environmental factors that can increase the risk of human cancer.

One advantage of the invention is that with the creation of neutrally buoyant, or near neutrally buoyant beads, due to a density similar to blood products, the beads remain naturally dispersed throughout blood or blood product, allowing substances in blood to be sorbed by the beads without the need, or with the reduced need, to mix or agitate the blood container.

DETAILED DESCRIPTION OF ILLUSTRATIVE EMBODIMENTS

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

Example 1: Overall Synthetic Approach

Figure 1:
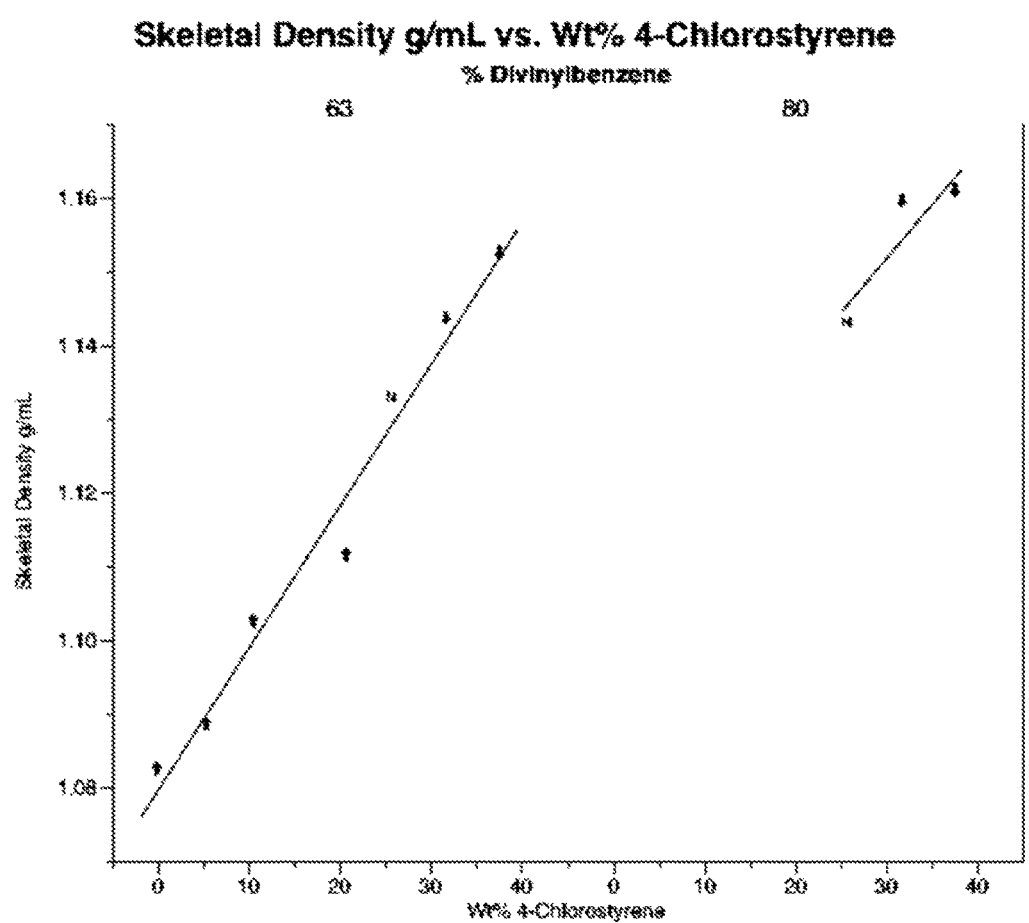
FIG. 1 shows the skeletal densities of the polymers created vs the weight percent of 4-chlorostyrene for Commercial 63% and 80% Divinylbenzene. This proves that higher weight percentages of 4-chlorostyrene yield greater skeletal densities of the final polymer. In the figure, down arrows (↓) represents a sinking bead, up arrow (↑) a floating bead and N is neutrally buoyant bead in Packed Red Blood Cells.
Figure 2:
FIG. 2 shows the distribution of neutrally buoyant beads in packed red blood cells.
Figure 2:
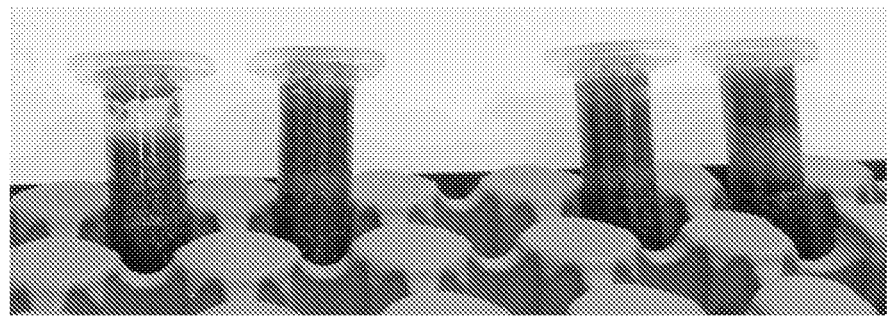
Figure 3:
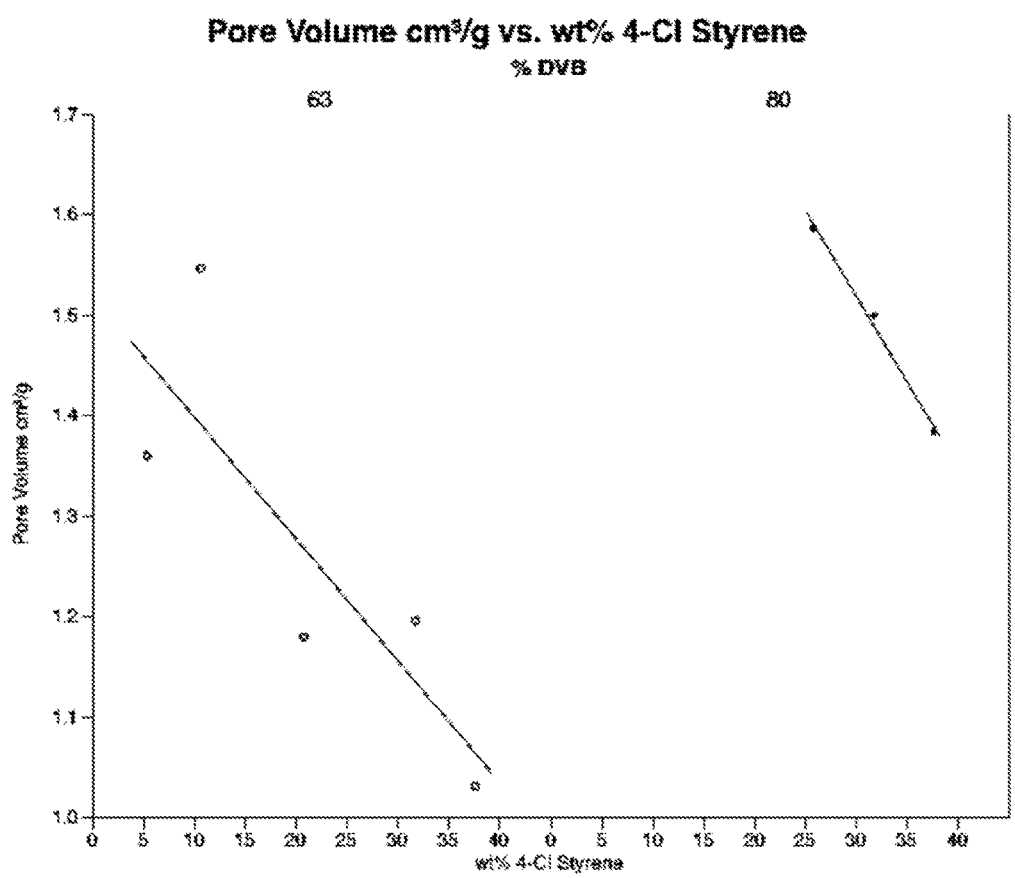
FIG. 3 displays the relationship between pore volume of the polymers created to the percent commercial Divinylbenzene and weight percent of 4-chlorostyrene used in the organic phase. This is used to illustrate that 80% divinylbenzene yielded higher pore volumes than 63% divinylbenzene with equal amounts of 4-chlorostyrene present.

In the pursuit of neutrally buoyant beads, early testing revealed that divinylbenzene based polymers, porous and solid beads, floated on packed red blood cells. Red blood cells (alone) have a density of 1.125 g/mL, while some of our divinylbenzene porous polymers have skeletal densities of 1.082 g/mL. In practice, bags of packed red blood cells contain more than the cells alone, including substances such as preservative (e.g. SAG), and residual plasma that can cause the density of packed red blood cells to vary from one bag to another. Plasma has a density of 1.025 g/mL. During our studies we found hematocrit values between 40% to 60%. Interestingly, poly 4-chlorostyrene has a density of 1.55 g/mL. Therefore, it was envisioned that at specific ratios, copolymerization of divinylbenzene and 4-chlorostyrene would yield a range of neutrally buoyant bead in packed red blood cells. Increasing amounts of 4-chlorostyrene was reacted with commercial 63% divinylbenzene as shown in FIG. 1 to yield a medium pore type polymer with varying densities. Structural density increased as predicted (as measured by a helium pycnometer). In FIG. 1, the down arrows (↓) represents a sinking bead, up arrow (↑) a floating bead and N is neutrally buoyant bead. Commercial 63% divinylbenzene yielded a neutrally buoyant bead at ~1.13 g/mL of skeletal density. FIG. 1 also incorporates commercial 80% divinylbenzene in decreasing skeletal density sequence to yield a neutrally buoyant bead. As displayed in FIG. 3, this sequence resulted in larger pore volumes, compared to 63% divinylbenzene, and was developed further. Two additional neutrally buoyant polymer types targeting different pore ranges using 80% divinylbenzene were synthesized via the same methodology. Examples 2, 3, and 4 are the three neutrally buoyant polymer types developed. Typical examples of how neutrally buoyant beads distribute in packed red blood cells are shown in FIG. 2.

Using these techniques, one skilled in the art can create beads with either a uniform density or a mixture of beads that vary in density, allowing some or all of the beads to be neutrally buoyant and dispersed throughout or in a band within blood products (e.g. packed red blood cells, platelets, etc.) in packed red blood cells of varying densities. Neutral buoyancy, or isodensity, or near neutral buoyancy allows beads to disperse throughout the blood or blood product with fewer beads that settle at the bottom of the blood or float at the surface of the blood. This is intended to enable the beads to efficiently remove BAMs without needing to agitate or mix the blood container. In some embodiments, a mixture of beads ranging in apparent density through modification of pore volume, pore density or combination thereof can provide a dispersion or bands of beads throughout the bag.

Examples 2-4: Sorbent Synthesis

Three porous polymeric sorbents are characterized for their pore structures and their syntheses are described in example 2, 3, and 4. The structural characterization is given in Example 5, 6 and 7. The polymers synthesized in these steps would then be placed into a suitable blood container The synthesis process consists of (1) preparing the aqueous phase, (2) preparing the organic phase, (3) carrying out the suspension polymerization, (4) purifying the resulting porous polymeric adsorbent product (work-up), and (5) addition of a hemocompatible coating.

Reactor Setup.

A 0.5 L kettle reactor was fitted with an over-head stirrer with a multi-level stirrer blade, a water cooled condenser, a thermocouple, and a bubbler. A gasket was installed between the top lid and bottom kettle. All unused ports were capped with the appropriate plug. Temperature was controlled with a heating mantle which was regulated by a temperature controller fitted with the above-mentioned thermocouple.

Polymerization.

Polyvinyl alcohol ("PVA") was dispersed in one half of the water charge at room temperature (RT) and then heated to 70° C. The remaining salts: MSP, DSP, TSP, & Sodium Nitrite (see Table 1) were then dissolved in the remainder of the water charge. The PVA solution and salts solution were each added to the reactor and heated to the desired reaction temperature (see Table 1) with stirring. The pre-mixed organic phase, including the initiator, was poured into the reactor onto the aqueous phase with the stirring speed set at the revolutions per minute ("rpm") for formation of appropriate droplet. Once the temperature reached the set-point, the reaction timer was set for 16 hours and started and the reaction was allowed to proceed.

Work-Up.

Final solvent level was marked on the reactor. After cooling, the solvent was siphoned out to the bead level. The reactor was filled to the mark with (RT) water and heated to between 50° C. to 70° C. and stirred for 30 minutes. Then it was allowed to settle for 3 to 5 minutes and the liquid was siphoned out to bead level. The beads were washed five times in this manner. The reactor was then filled to the mark with RT methanol, if applicable (see Table 1), and stirred at RT for 5 minutes. Beads were allowed to settle for 3 to 5 minutes. Beads were washed 3 times in this manner. The polymer was steam stripped for 8 hours. After the steam strip was completed, the polymer was rewet in isopropyl alcohol and then sieved with purified water to the desired particle size. The polymer was then dried in an oven at 100° C.

This process resulted in a clean, dry adsorbent in the form of spherical, porous polymer beads.

The polymer could then be modified for greater hemocompatibility via the procedure from U.S. Pat. No. 6,114,466.

TABLE 1

Synthesis conditions for neutrally buoyant polymers

|  | Example 2 SFA-102-155 | Example 3 RJR-100-112 | Example 4 RJR-100-110 |
|---|---|---|---|
| Run Conditions |  |  |  |
| Kettle Size | 0.5 | 0.5 | 0.5 |
| Reaction Temperature (° C.) | 80 | 87 | 87 |
| Item | Charge, g | Charge, g | Charge, g |
| Aqueous Phase Charges |  |  |  |
| Ultrapure Water | 231.26 | 231.26 | 231.26 |
| Polyvinyl Alcohol (PVA) | 0.68 | 0.68 | 0.68 |
| Monosodium Phosphate (MSP) | 0.71 | 0.71 | 0.71 |
| Disodium Phosphate (DSP) | 2.36 | 2.36 | 2.36 |
| Trisodium Phosphate (TSP) | 1.47 | 1.47 | 1.47 |
| Sodium Nitrite | 0.01 | 0.01 | 0.01 |
| Total | 236.49 | 236.49 | 236.49 |
| Organic Phase Charges |  |  |  |
| Divinylbenzene (DVB) (80%) | 66.4 | 64.97 | 101.57 |
| 4-Chlorostyrene | 23.1 | 23.1 | 35.81 |
| Toluene | 55.78 | 0.00 | 0.00 |
| Isooctane | 64.07 | 0.00 | 0.00 |
| Cyclohexanol | 0.00 | 151.03 | 102.93 |
| Benzoyl Peroxide (BPO) (97%) | 0.90 | 0.90 | 0.90 |
| Total, w/o BPO | 209.35 | 239.10 | 240.31 |
| Work-Up |  |  |  |
| Methanol Washes | N/A | 3 | 3 |

Example 5: Pore Structure Characterization

Figure 4:
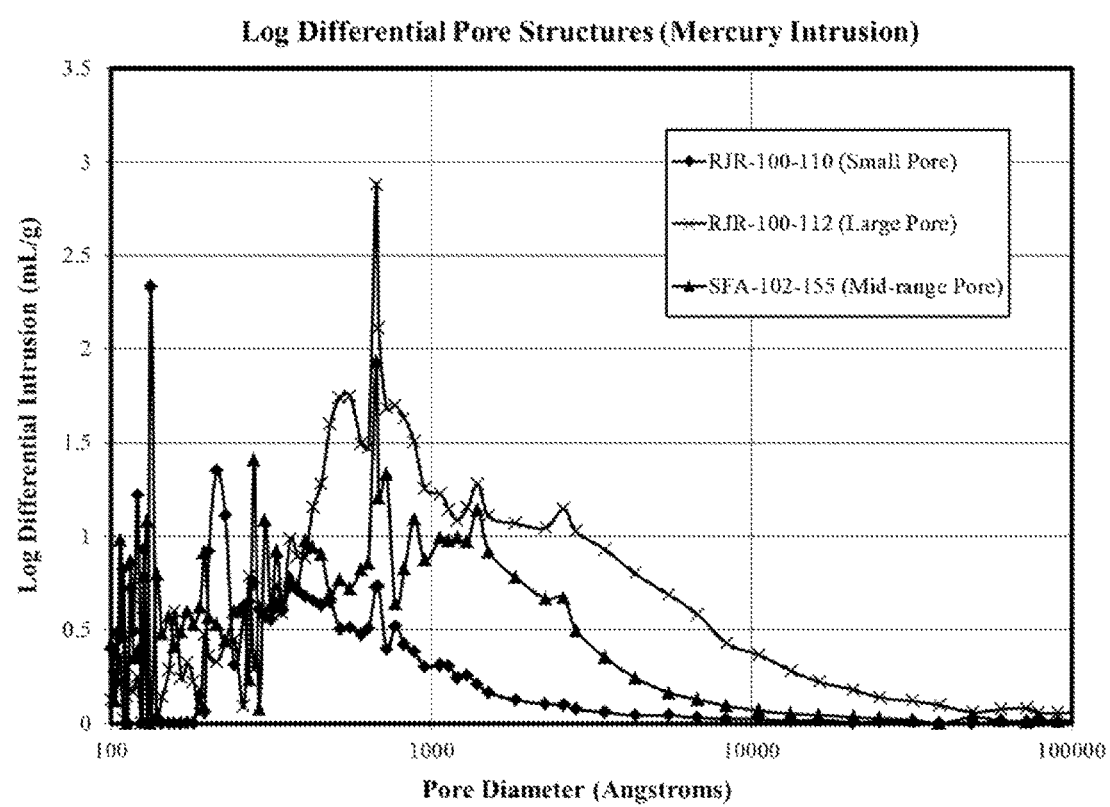
FIG. 4 is a graph which shows pore volume as a function of pore diameter based on mercury intrusion. A high pore volume at a given pore diameter means there are many pores of that size; a lower pore volume at a given pore diameter means few pores of the given size.
Figure 5:
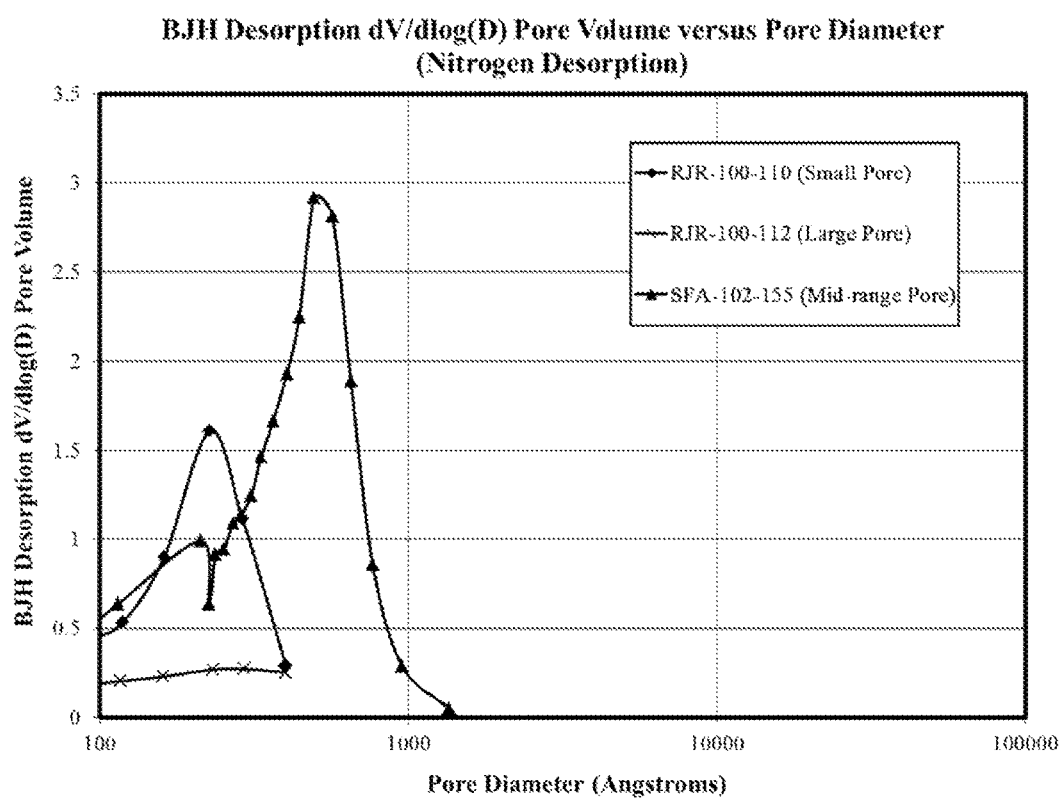
FIG. 5 is a graph which shows pore volume as a function of pore diameter based on nitrogen desorption. A high pore volume at a given pore diameter means there are many pores of that size; a lower pore volume at a given pore diameter means few pores of the given size.
Figure 7:
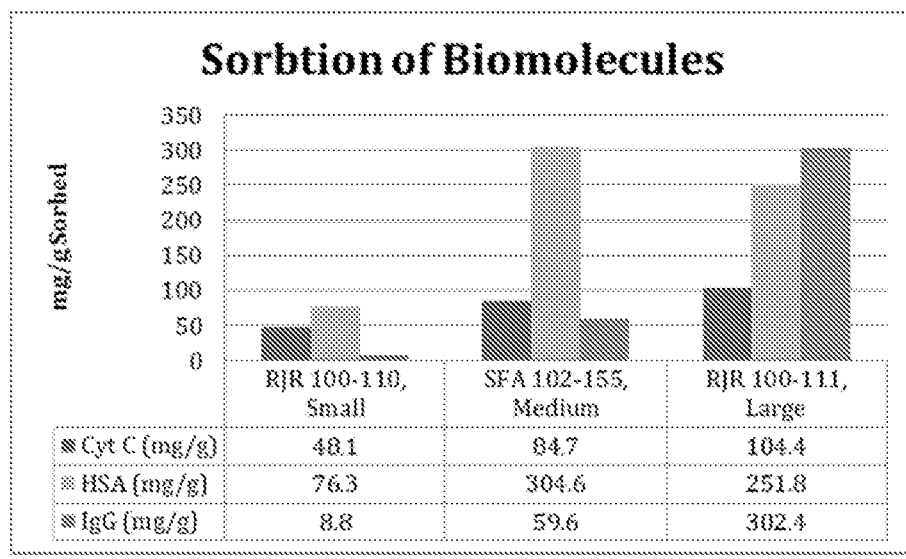
FIG. 7 shows the variation in the sorption of biomolecules for the three different sized polymers which were created.

The pore structures of the sorbent polymers were analyzed with both a Micromeritics AutoPore IV 9500 V1.09 Mercury Penetrometer (Hg Intrusion instrument) or a Micromeritics ASAP 2010 instrument ($N_2$ Desorption) to show the existence of large pores and small pores. The results are provided in FIGS. 4 and 5 where the pore volume is plotted as a function of the pore diameter. Varying pore structure allows for polymers to sorb a range of different harmful byproducts in blood as shown in FIG. 7.

Examples 6 and 7: Density Characterization

For each polymer made, the density was determined using two different techniques. The first technique used was helium pycnometry. A Micromeritics AccuPyc 1330 for 1 cm³ samples, was used to determine the skeletal density (density of the polymer backbone) of each polymer.

A second technique was also needed because neutral buoyancy is defined by the Archimedes principal where an object is buoyed up by a force equal to the weight of the liquid displaced by the object. In the case of a porous polymer bead this represents a unique situation where the composite porous bead density is a function of the skeletal density and medium occupied in the bead pores.

The relationship can be expressed as follows in equation 1:

$$\rho_{bead\text{-}apparent}=(\%\text{ volume non porous})*\rho_{skeletal}+(\%\text{ volume porous})*\rho_{suspension\ media} \quad \text{Equation 1}$$

In the case of a neutrally buoyant porous polymer:

$$\rho_{bead\ apparent}=\rho_{suspension\ media}\text{ (assumes no appreciable sorption of solutes)} \quad \text{Equation 2}$$

Figure 6:
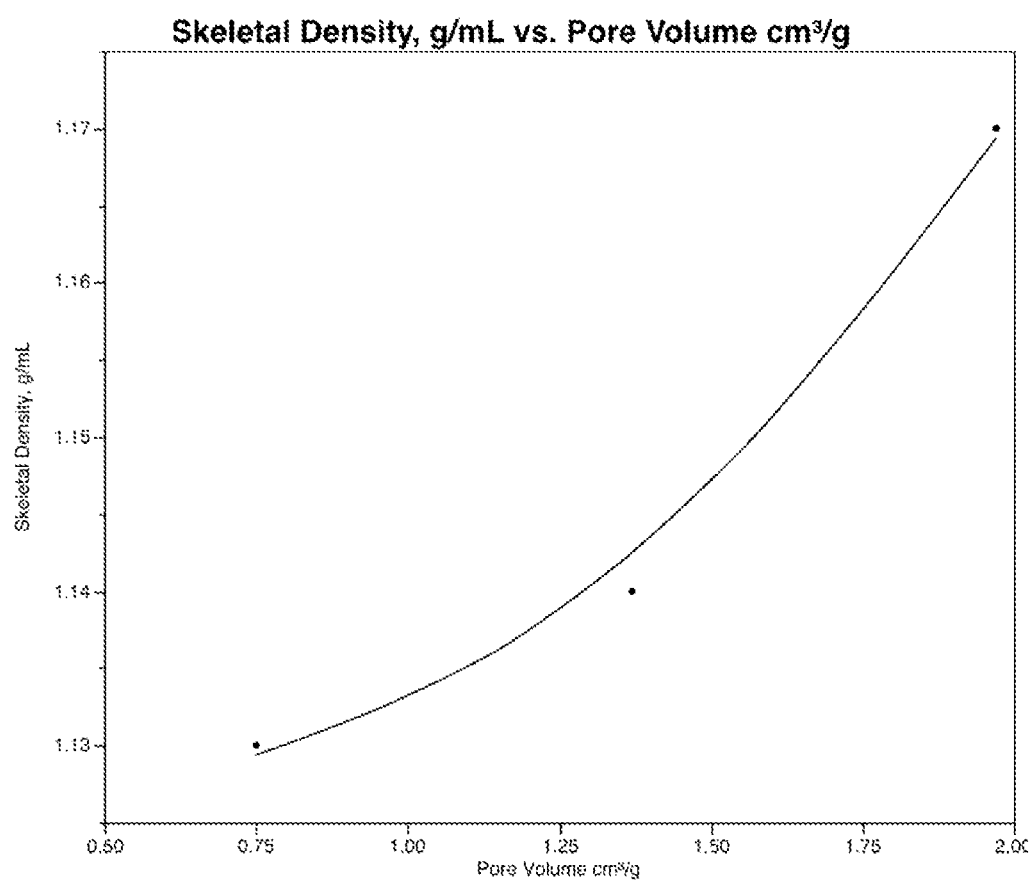
FIG. 6 illustrates that in order to create neutrally buoyant polymer beads, as the pore volume of the polymer increases, the skeletal density of the polymer must also increase.

The second technique, which determined the apparent density, was a simple lab test where the polymer was placed in blood so that neutral buoyancy could be determined visually. FIG. 2, which is the end result of this second technique, shows that the beads are suspended in the middle of the sample of blood so they are determined to be neutrally buoyant. The polymers RJR 100-110, SFA 102-155, and RJR 100-112 were all neutrally buoyant in Packed RBC's; therefore, the apparent density was nearly equivalent to the Packed RBC's. It should be noted, that increases in pore volume required increases in skeletal density to offset potential reduction in apparent density due to lower density preservatives (SAG for example) and plasma entering the pores. This is demonstrated in FIG. 6.

Example 8: Sorption of Biomolecules

Non-competitive Equilibrium Isotherms were run on RJR 100-110, SFA 102-155, and RJR 100-112 in buffer solution to evaluate the sorbtion capacity for Cytochrome c (Cyt C, 12 kDa), Human Serum Albumin (HSA, 67 kDa) and Immunoglobulin G (IgG, 150 kDa). Cyt C, HSA, and IgG are acting as molecular weight surrogates for the Biologically Active Molecules (BAM)s. Each was individually tested and all values were measured by UV/Vis Absorbance and reported as mg of protein sorbed/g of dry polymer.

What is claimed:

1. A device comprising a plurality of porous sorbent polymeric beads for sorbing impurities from blood, said beads comprising a biocompatible polymer comprising particles having a diameter in the range for 0.1 micrometer to 2 centimeters and has a pore structure that the total pore volume of pore size in the range of 50 Å to 40,000 Å is greater than 0.5 cc/g to 5.0 cc/g dry polymer, and wherein (a) said plurality of beads being housed in a suitable container intended for storage of blood or blood product wherein said beads would be in direct contact with said blood or blood product or (b) said plurality of beads being contained in cartridge that is used (i) to filter the blood or blood product at time of collection as said or blood product is placed in a bag for storage or (ii) at the point of use during transfusion when said blood or blood product is transfused from the bag to a patient, and
wherein said beads comprising divinylbenzene and 4-chlorostyrene and having a skeletal density in the range of from about 1.0 g/ml to about 1.3 g/ml.

2. The device of claim 1, wherein the sorbent has a skeletal density in the range of from about 1.1 g/ml to about 1.3 g/ml.

3. The device of claim 1 wherein the sorbent has a skeletal density that is substantially the same as the density of the blood or blood product.

4. The device of claim 1, wherein said sorbent polymeric bead having a pore structure such that the total pore volume of pore size in the range of 50 A to 40,000 A is greater than 0.5 cc/g to 5.0 cc/g dry sorbent; wherein the ratio of pore volume between 50 A to 40,000 A (pore diameter) to pore volume between 100 A to 1,000 A (pore diameter) of the sorbent is smaller than 3:1.

5. The device of claim 1, wherein said sorbent comprises cross-linked polymeric material derived from the reaction of a cross-linker with divinylbenzene and 4-chlorostyrene and further comprises one or more of the following polymerizable monomers: styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, 2-chlorostyrene, 3-chlorostyrene, 2,6-dichlorostyrene, 4-vinylbenzyl chloride, 2-bromostyrene, 3-bromostyrene, 4-bromostyrene, 2-fluorostyrene, 3-fluorostyrene, 4-fluorostyrene, 2-trifluoromethylstyrene, 3-trifluoromethylstyrene, 4-trifluoromethylstyrene, 2,3,4,5,6-pentafluorostyrene, 4-vinyl-18-crown-6 benzene, 2-chloroacrylate, 2,2,2-trifluoromethylmethacrylate, 2-trifluoromethylacrylate, methyl 2-(chloromethyl)acrylate, methyl 2-(bromomethyl)acrylate, 1H, 1H, 2H, 2H-heptadecafluorodecyl acrylate, vinyl chloroacetate, and 2-chloroethyl vinyl ether.

6. The device of claim 1, wherein said crosslinking agent is selected from divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof.

7. The device of claim 1, wherein said sorbent comprises a hemocompatible surface comprises hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly-(diethylaminoethyl acrylate), poly(vinyl alcohol), poly(N-vinylpyrrolidinone), salts of poly(methacrylic acid), salts of poly(acrylic acid) or copolymers of mixtures thereof, wherein said hemocompatible surface is chemically bound to the cross-linked polymeric material.

8. A method of treating stored blood and blood products maximizing shelf life and/or minimizing transfusion related complications by removing undesirable molecules in the blood and blood products milieu, said removing comprising contacting said stored blood or blood products with the device of claim 1.

9. The methods of claim 8, wherein said undesirable molecules are biologically active molecules (BAMs), biological response modifiers (BRMs), products of hemolysis, products of membrane or cellular degradation, toxins, drugs, antibodies, prions and similar molecules found in stored blood and blood products.

10. The method of claim 9, wherein the biologically active molecules or biological response modifiers comprise inflammatory mediators and stimulators selected from cytokines, nitric oxide, thromboxanes, leukotrienes, platelet, activating factor, prostaglandins, glycoproteins, kinins, kininogens, complement factors, cell-adhesion molecules, superantigens, monokines, chemokines, interferons, free radicals, proteases, arachidonic acid metabolites, prostacyclins, beta endorphins, myocardial depressant factors, anandimide, 2-arachadonylglycerol, tetrahydrobiopterin, serotonin, histamine, bradykinin, soluble CD40 ligand, bioactive lipids, oxidized lipids, hemoglobin, red cell particulates, membrane or cellular components, growth factors, glycoproteins, prions, toxins, endotoxins, drugs, vasoactive substances, foreign antigens, and antibodies.

11. The method of claim 9 where undesirable molecules are antibodies.

12. The method of claim 8, wherein said biocompatible polymer is hemocompatible.

13. The method of claim 8, wherein said sorbent is supplied as a slurry, or suspension, or dry powder or other dry particulate capable of being wetted.

14. The method of claim 1, wherein the sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 100 Å to 1,000 Å (pore diameter) of the sorbent is smaller than 3:1.

15. The method of claim 14, wherein the undesirable molecule is a toxin having a molecular weight that is equal to or less than about 50,000 Daltons.

16. The method of claim 8, wherein the sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 1,000 Å to 10,000 Å (pore diameter) of the sorbent is smaller than 2:1.

17. The method of claim 16, wherein the undesirable molecule is a toxin having a molecular weight in the range of from about 100 Daltons to about 450,000 Daltons.

18. The method of claim 8 wherein the sorbent has a pore structure such that the total pore volume of pore size in the range of 50 Å to 40,000 Å is greater than 0.5 cc/g to 5.0 cc/g dry sorbent; wherein the ratio of pore volume between 50 Å to 40,000 Å (pore diameter) to pore volume between 10,000 Å to 40,000 Å (pore diameter) of the sorbent is smaller than 3:1.

19. The method of claim 18, wherein the undesirable molecule is a toxin having a molecular weight that is equal to or less than about 1,000,000 Daltons.

20. The method of claim 8, wherein said sorbent is produced using at least one of suspension, seed, dispersion, precipitation, multistage, membrane/microchannel emulsification and microfluidic polymerizations.

21. The method of claim 8, wherein said sorbent comprises cross-linked polymeric material derived from the reaction of a cross-linker with divinylbenzene and 4-chlorostyrene and further comprises one or more of the following polymerizable monomers: styrene, ethylstyrene, acrylonitrile, butyl methacrylate, octyl methacrylate, butyl acrylate, octyl acrylate, cetyl methacrylate, cetyl acrylate, ethyl methacrylate, ethyl acrylate, vinyltoluene, vinylnaphthalene, vinylbenzyl alcohol, vinylformamide, methyl methacrylate, methyl acrylate, 2-chlorostyrene, 3-chlorostyrene, 2,6-dichlorostyrene, 4-vinylbenzyl chloride, 2-bromostyrene, 3-bromostyrene, 4-bromostyrene, 2-fluorostyrene, 3-fluorostyrene, 4-fluorostyrene, 2-trifluoromethylstyrene, 3-trifluoromethylstyrene, 4-trifluoromethylstyrene, 2,3,4,5,6-pentafluorostyrene, 4-vinyl-18-crown-6 benzene, 2-chloroacrylate, 2,2,2-trifluoromethylmethacrylate, 2-trifluoromethylacrylate, methyl 2-(chloromethyl)acrylate, methyl 2-(bromomethyl)acrylate, 1H, 1H, 2H, 2H-heptadecafluorodecyl acrylate, vinyl chloroacetate, and 2-chloroethyl vinyl ether.

22. The method of claim 21, wherein said crosslinking agent is selected from divinylbenzene, trivinylbenzene, divinylnaphthalene, trivinylcyclohexane, divinylsulfone, trimethylolpropane trimethacrylate, trimethylolpropane dimethacrylate, trimethylolpropane triacrylate, trimethylolpropane diacrylate, pentaerythrital dimethacrylates, pentaerythrital trimethacrylates, pentaerythrital, tetramethacrylates, pentaerythritol diacrylates, pentaerythritol triiacrylates, pentaerythritol tetraacrylates, dipentaerythritol dimethacrylates, dipentaerythritol trimethacrylates, dipentaerythritol tetramethacrylates, dipentaerythritol diacrylates, dipentaerythritol triacrylates, dipentaerythritol tetraacrylates, divinylformamide and mixtures thereof.

23. The method of claim 8, wherein said sorbent comprises a hemocompatible surface comprises hydroxyethyl cellulose, hydroxypopyl cellulose, poly(hydroxyethyl methacrylate), poly(hydroxyethyl acrylate), poly(hydroxypropyl methacrylate), poly(hydroxypropyl acrylate), poly(dimethylaminoethyl methacrylate), poly(dimethylaminoethyl acrylate), poly(diethylamimoethyl methacrylate), poly-(diethylaminoethyl acrylate), poly(vinyl alcohol), poly(N-vinylpyrrolidinone), salts of poly(methacrylic acid), salts of poly(acrylic acid) or copolymers of mixtures thereof, wherein said hemocompatible surface is chemically bound to the cross-linked polymeric material.

24. The method of claim 8, wherein said biocompatible polymer is modified with ligands that specifically or non-specifically bind reactive biomolecules.

25. The method of claim 8, wherein said sorbent is contained in a blood container with said blood or blood products.

26. The method of claim 8, wherein said sorbent is contained in cartridge that may be used at time of collection as blood is placed in the bag for storage or at the point of use during transfusion.

27. The method of claim 8, wherein said sorbent is in a suitable container to hold blood and in direct contact with blood and blood products but incapable of escaping from the container.

28. The method of claim 8, wherein said sorbent is in a suitable container to hold blood and separated from the blood by a permeable membrane or barrier allowing fluid but not cells to interact with the polymer.

29. The method of claim 8, wherein said sorbent is structurally an integral part of the container material homogeneously dispersed throughout the container walls, or discretely sealed in multiple areas of the container providing zones of direct contact with the blood or blood products, or coated, deposited or attached to the inside walls of the container in direct contact with the blood or blood products.

30. The method of claim 8, wherein the sorbent has a skeletal density in the range of from about 1.1 g/ml to about 1.3 g/ml.

31. The method of claim 8, wherein the sorbent has a skeletal density that is substantially the same as the density of the blood or blood product.

32. The method of claim 20, wherein said seed polymerization method including seed of polymers utilizes a combination of 100% hetero atom monomers and non-hetero atom monomers such that the combination can lead to a neutrally buoyant system.

33. The method of claim 8, wherein said beads are placed in a container where, due to a density similar to blood products, said bead remain naturally dispersed throughout blood or blood product, allowing undesirable molecules in blood to be sorbed by the beads without the need to mix or agitate the container.

34. The method of claim 8, wherein said sorbent is in a suitable container to hold blood and in direct contact with blood and blood products but incapable of escaping from the container at a level that meets USP particulate as specified in monograph 65.

35. The method of claim 8 wherein said beads are placed in a container where, due to a density similar to blood products, said bead remain naturally dispersed throughout blood or blood product, allowing undesirable molecules in blood to be sorbed by the beads without the need to mix or agitate the container.

36. The method of claim 8, wherein the transfusion related complications comprise one or more of fever, transfusion-related acute lung injury (TRALI), transfusion associated dyspnea (TAD), and allergic reactions.

\* \* \* \* \*